United States Patent

He et al.

[11] Patent Number: 6,114,291
[45] Date of Patent: *Sep. 5, 2000

[54] CAST MELT BAR COMPOSITIONS COMPRISING HIGH LEVELS OF LOW MOLECULAR WEIGHT POLYALKYLENE GLYCOLS

[75] Inventors: Mengtao He, Wayne; James Joseph Dalton, Cliffside Park, both of N.J.; Kennard Daniels, Danbury, Conn.; Georgia Shafer, Carteret, N.J.; Michael Massaro, Congers, N.Y.

[73] Assignee: Lever Brothers Company division of Conopco, Inc., New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 09/015,558

[22] Filed: Jan. 29, 1998

Related U.S. Application Data

[63] Continuation-in-part of application No. 08/733,035, Oct. 16, 1996, abandoned.

[51] Int. Cl.[7] .............................. A61K 7/50; C11D 17/00
[52] U.S. Cl. .......................... 510/152; 510/153; 510/155; 510/156
[58] Field of Search ................................... 510/141, 142, 510/145, 151, 152, 153, 155, 156

[56] References Cited

U.S. PATENT DOCUMENTS

| | | | |
|---|---|---|---|
| 5,262,079 | 11/1993 | Kacher et al. | 252/112 |
| 5,520,840 | 5/1996 | Massaro et al. | 510/152 |
| 5,540,854 | 7/1996 | Fair et al. | 510/152 |

*Primary Examiner*—Necholus Ogden
*Attorney, Agent, or Firm*—Ronald A. Koatz

[57] ABSTRACT

The present invention relates to skin cleansing bar composition in which polyalkylene glycols of very specific molecular weights are used to define compositions which are mild, foam well and provide consumer-desired sensory profiles. A significant amount of these specific PEGs must be incorporated into the bar to deliver these desired effects. To properly process such a bar composition, the cast-melt method is the preferred technique.

10 Claims, 3 Drawing Sheets

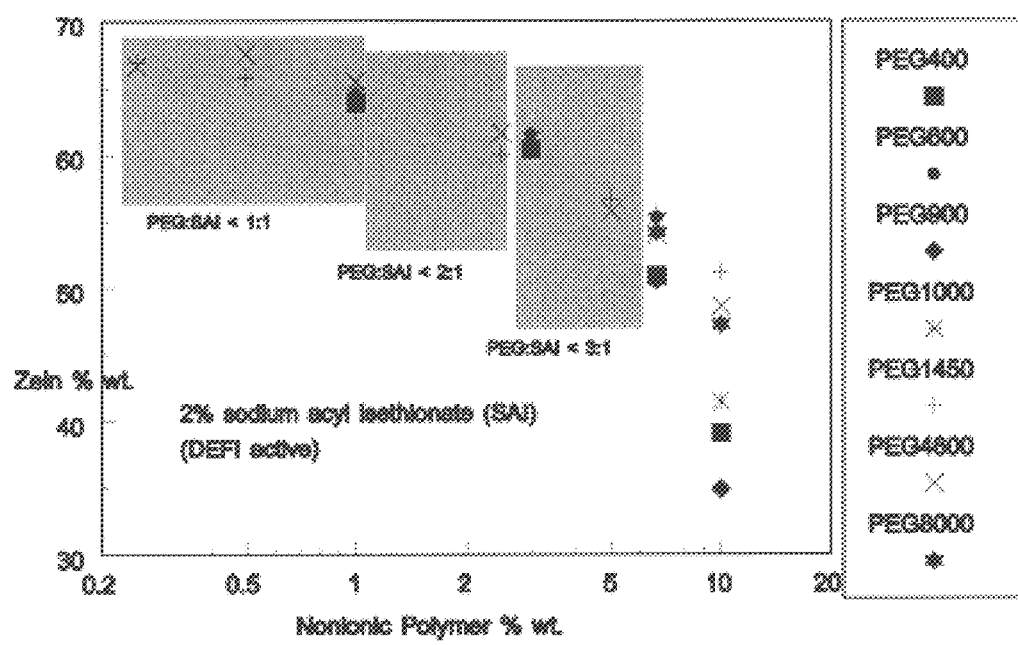

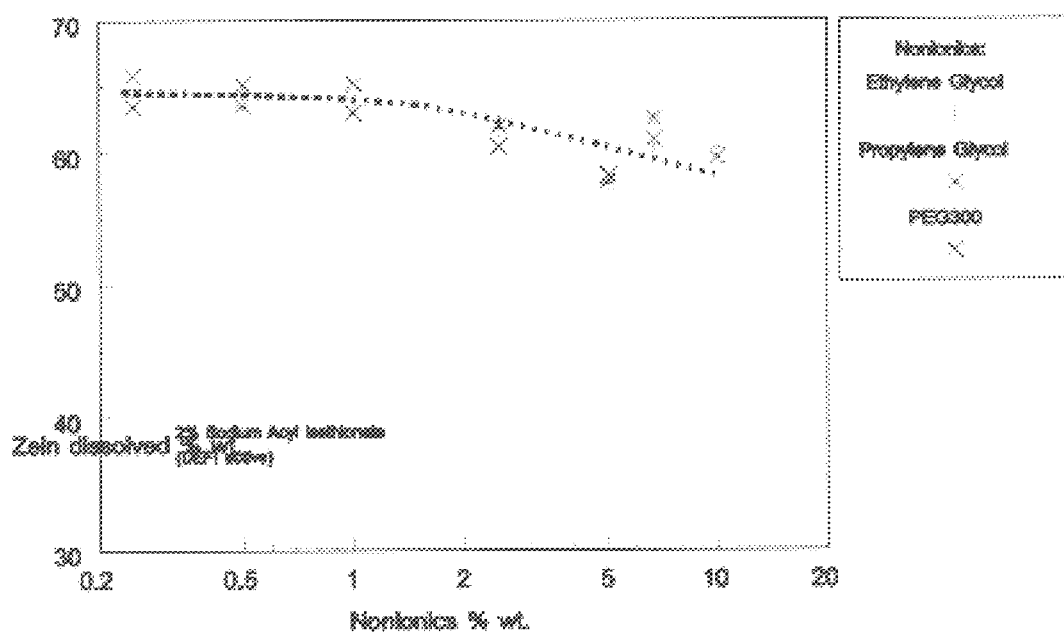

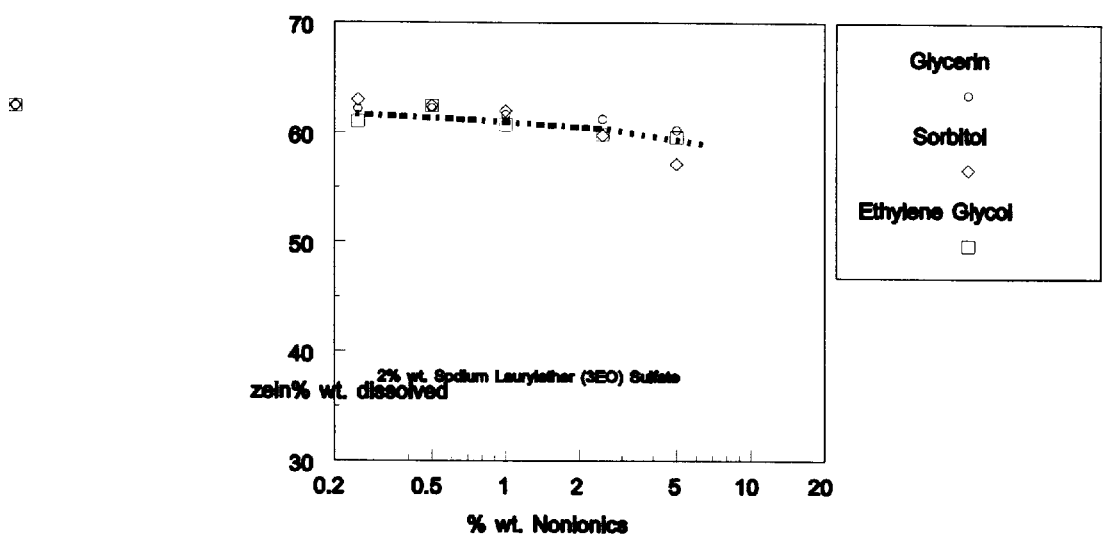

CAST MELT BAR COMPOSITIONS COMPRISING HIGH LEVELS OF LOW MOLECULAR WEIGHT POLYALKYLENE GLYCOLS

RELATED APPLICATIONS

The present application is a Continuation-in-part of U.S. Ser. No. 08/733,035, filed Oct. 16, 1996 now abandoned.

FIELD OF THE INVENTION

The present invention relates to skin cleansing bar compositions preferably formed by cast melt method. These bars are extremely mild, foam well and provide consumer-desired sensory properties.

BACKGROUND

Personal washing bars are constantly moving toward milder formulations that ultimately will provide some enhanced skin care, for example, minimizing levels of skin irritation and enhancing moisturization. It is desirable to have a bar composition that carries a significant amount of emollient oily liquid that provides positive sensory cues to many consumers. To properly process such a bar composition, cast-melt is the preferred technique.

It is a challenge to find an economical bulk chemical which can function as a bar filler/binder that enhances skin mildness or moisturization, promotes bar lather performance and facilitates bar processing. For example, solid polyalkylene glycols (e.g., polyethylene glycols (PEG) having molecular weight above 2000) are effective bar structurants and they do not defoam. However, in comparison to a PEG having a lower molecular weight, they provide much less oily skin feel which signals moisturization to many consumers, and they are less readily miscible with long chain fatty acid soaps that are used as gelling agents in the subject invention. Solid fatty acids, on the other hand, can effectively structure bar but tend to defoam. Paraffin waxes defoam if included in a bar at relatively high levels (i.e., greater than 25% wt. total composition), especially in the presence of hydrophobic emollient oils.

In the subject invention, applicants have formulated relatively high levels of low molecular weight polyalkylene glycols (e.g., polyethylene glycol having molecular weight of 300 to below 1500, preferably about 350 to 1450, more preferably 350 to 1400, more preferably 350 to 1300) in a synthetic detergent bar using the cast melt technology. In-vivo and in-vitro data showed that, only at high levels of addition (polyethylene glycol to anionic weight ratio at 1:1 and above) do these low MW PEGs significantly mitigate the irritation potential of commonly used anionic surfactants. Unlike solid PEGs with molecular weight greater than 1500, the low molecular weight PEGs are more readily miscible with long chain fatty acid soaps that are the gelling agents of this invention, and therefore are a significant component of the immobilized liquid fraction of these bars. It is this liquid fraction that readily dissolves upon use providing the benefits of enhanced skin feel, mildness and lather. As an additional benefit, the low molecular weight PEGs enhance desired lather properties to a skin cleanser.

Thus using high levels of these relatively low molecular weight materials, applicants were able to obtain bars which simultaneously (1) provided desired user and processing properties (2) lathered well and (3) were less irritating.

The use of polyalkylene glycol (e.g., polyethylene glycol) in personal washing bar compositions is not itself new.

U.S. Pat. No. 3,312,627, to D. Hooker, for example, teaches a bar composition containing 30–70% polyethylene glycol (PEG) as bar structurant for a nonionic formulation basically free of anionic detergents. The PEG used in this invention has a molecular weight above 4000 Dalton, which is significantly higher than the MW claimed for the PEGs applied in the subject invention (less than 1500, preferably greater than 300 to about 1450 and below). In contrast to the subject invention, the referred patent used significantly higher level of high MW PEG in total bar composition. Further, the PEG/anionic surfactant ratio is not important in this patent since it refers to a primarily nonionic formulation.

World Patent Application No. 93/07245 to F. Moran, B. O'Briain and D. Moran (assigned to NEPHIN) teaches a shampoo bar composition containing 12–20% synthetic detergents and 70–80% PEGs with molecular weight between 5000 and 10,000. An embodiment of the invention includes a softening PEG with molecular weight between 100 and 800 (preferably 1–8% wt. total composition). In contrast to the subject invention, the referred patent application used a significant level (70–80%) of high MW PEGs in total bar composition. The referred patent used significantly less amount of low MW PEG than used in the subject invention.

In applicant's copending U.S. Ser. No. 08/594,363, Continuation of U.S. Ser. No. 08/213,287, entitled "*Synthetic Detergent Bar and Manufacture Thereof*", to J. Chambers et al., there is taught a bar containing 10–60% synthetic surfactants and 10–60% PEG as structurant. The PEG used has a range of melting temperatures between 40° C. and 100° C., and a range of molecular weight between 1500 and 10,000. This molecular weight makes PEG a solid at room temperature. The PEG molecular weight used is above that claimed (less than 1500, preferably about greater than 300 to about 1450 and below) by the subject invention. Also the referred patent application does not teach PEG/anionic ratio of at least 1:1 that is relevant to the mildness enhancement, a criticality of the subject invention.

U.S. Pat. No. 5,520,840 to M. Massaro et al. teaches a skin cleansing bar composition containing 10–60% of synthetic surfactant, 10–60% water soluble structurant (e.g., PEG) with having a range of melting points between 40° C. and 100° C., and 1–25% water soluble starch such as maltodextrin. Again, the molecular weight of the PEGs used (i.e., above 1500) is above that claimed for the subject invention. Also the referred patent application does not teach a PEG/anionic ratio of at least 1:1 that is relevant to the mildness enhancement, a criticality of the subject invention.

U.S. Pat. No. 2,287,484 to Lundberg teaches a bar made by a closed die molding technique which comprises 35–70% of anionic synthetic surfactant and 22–50% fatty acid. The bar also may contain up to 10% ethylene and di-ethylene glycols as additives. As found by the subject invention, the ethylene and di-ethylene glycols are not as effective as low MW PEGs (MW above 300) in reducing the skin irritation of anionic surfactants. Also the referred patent does not teach a PEG/anionic surfactant weight ratio of at least 1:1 that is relevant to the mildness enhancement, a criticality of the subject invention.

Applicants' copending application Ser. No. 08/662,394, filed Jun. 12, 1996 teaches a mild bar composition containing 10–60% synthetic detergents, 10–50% high molecular weight PEG with melting point above 40° C. and 0.1 to 10% low molecular weight PEG (melting point below 40° C.) as processing aid. The application claims the use of relatively low levels of low MW PEG as a lubricant to aid the extrusion process. This is significantly different from the art of the subject invention, which formulated relatively high levels of low MW PEG (e.g., >10% wt. total composition) into a bar as a moisturizer. Also the referred patent application did not specify the PEG/anionic surfactant weight ratio, which is a criticality of the subject invention to achieve superior skin mildness.

U.S. Pat. Nos. 5,262,079 and 5,227,086 to M. Kacher, J. Taneri, D. Quiram, D. Schmidt and M. Evans teach a framed cleansing bar composition containing 5–50% of a mixture of free and neutralized monocarboxylic acid, 15–65% synthetic anionic and nonionic bar firmness aid and 15–55% water. The bar firmness aid consists of 5–50% synthetic surfactants and 0–40% polyethylene glycol or polypropylene glycol with MW ranging from approximately 44 to 10,000 Dalton. The referred patents do not teach or suggest use of PEGS with MW between 400 and 1500 with specific PEG/anionic surfactant weight ratios to achieve both enhanced cast-melt processibility and mildness enhancement. Further, to obtain the desired bar user properties (i.e., mush and hardness) the applicants of the subject invention include only 2–10% wt. water in the bar compositions claimed, which is significantly below the 15–55% water claimed by the referred patents.

Finally, applicants are concurrently filing an application entitled *"Pourable Cast Melt Bar Compositions Comprising Low Levels of Water and Minimum Ratios of Polyol to Water"*. The subject invention is made by the same cast melt methodology. However, the related application is not directed to specific compositions wherein high levels of polyalkylene glycol with molecular weight between 400 and 1,500 are used and ratio of polyalkylene glycol to anionic surfactant is at least 1:1.

BRIEF SUMMARY OF THE INVENTION

The present invention relates to bar compositions in which alkylene glycols (e.g., polyethylene glycols) of very specific molecular weight range (high enough molecular weight to mitigate harshness effect of anionic, but low enough MW to provide the desired sensory profile and facilitate the cast-melt processing) are used and ratio of alkylene glycol to anionic is maintained at least 1:1 and higher. Such compositions are mild, foam well and provide consumer desired sensory profiles.

More specifically, the invention comprises:

(1) 2 to 35%, preferably 10 to 30% by wt. total composition synthetic anionic surfactant;

(2) 0 to 20% by wt. total composition surfactant selected from the group consisting of amphoteric, zwitterionic nonionic and mixtures thereof; preferably amphoteric and zwitterionic surfactants comprise 2 to 15% by wt. total composition;

(3) 10% by 70% by wt. total composition of a polyalkylene glycol or mixture of polyalkylene glycol compounds having MW greater than 300 to less than about 1500, preferably grater than 300 to about 1450 and below, more preferably 350 to 1400, more preferably above about 400 to about 1300 and below. Especially preferred embodiments have MW of about 1000 and below;

the weight ratio of the polyalkylene glycol to the anionic surfactant being at least 1:1, preferably 2:1 and greater;

(4) about 0% to 35% by wt. of solid structuring aids and fillers selected from the group consisting of (i) polyalkylene glycols having MW of 2500 to 10,000 and MP of about 55° to 65° C.; (ii) preferably straight chain, preferably saturated $C_8$ to $C_{24}$ free fatty acids; (iii) preferably straight chain, preferably saturated $C_8$ to $C_{20}$ alkanols; (iv) water soluble starches (e.g., maltodextrin);

(5) about 1% to 20% by wt. gelling agent; and (6) about 2% to 10% by wt. water.

BRIEF DESCRIPTION OF DRAWINGS

FIG. 1 is a graph showing that polyethylene glycol with molecular weight of 400 and above significantly reduce the amount of zein dissolved by acyl isethionate (i.e., is less harsh) when weight ratio of PEG to isethionate is above 1:1, preferably above 2:1.

FIG. 2 shows that, at molecular weight below 400, PEGs or other water soluble nonionic monomer (e.g. ethylene glycol, propylene glycol) do not reduce the amount of zein dissolved by isethionate.

FIG. 3 shows that at molecular weight below 400, PEGs or other water soluble nonionic monomer do not reduce the amount of zein dissolved by sodium lauryl ether.

DETAILED DESCRIPTION OF THE INVENTION

The present invention relates to compositions in which alkylene glycols within a very specific molecular weight range (high enough to mitigate harshness effect of anionic surfactant, but low enough MW to provide consumer-desired sensory profile and facilitate the cast-melt processing) are used at a minimum ratio of alkylene glycol to anionic to provide compositions which are (1) mild, (2) maintain good foam profile and (3) provide both consumer-desired sensory profiles (i.e., due to lower molecular weight) and processing benefits.

More specifically, the composition comprises:

(1) 2 to 35%, preferably 10 to 30% by wt. total composition synthetic anionic surfactant;

(2) 0 to 20% by wt. total composition surfactant selected from the group consisting of amphoteric, zwitterionic nonionic and mixtures thereof; preferably amphoteric and zwitterionic surfactants comprise 2 to 15% by wt. total composition;

(3) 10% by 70% by wt. total composition of a polyalkylene glycol or mixture of polyalkylene glycol compounds having MW greater than 300 to less than 1500, preferably greater than 300 to about 1450 and below, more preferably 350 to 1400, more preferably above about 400 to about 1300 and below. Especially preferred embodiments have MW of about 1000 and below;

the weight ratio of the polyalkylene glycol to the anionic surfactant being at least 1:1, preferably 2:1 and greater;

(4) about 0% to 35% by wt. of solid structuring aids and fillers selected from the group consisting of (i) polyalkylene glycols having MW of 2500 to 10,000 and MP of about 55° to 65° C.; (ii) preferably straight chain, preferably saturated $C_8$ to $C_{24}$ free fatty acids; (iii) preferably straight chain, preferably saturated $C_8$ to $C_{20}$ alkanols; (iv) water soluble starches (e.g., maltodextrin);

(5) Further, because the high levels of low MW polyalkylene glycol are in the form of liquid or paste, about 1% to 20% by weight total composition gelling agents, as described more specifically below, are used to enhance bar integrity; and (6) about 2% to 10% by weight total composition water.

Synthetic Non Soap Surfactant

The surfactant system of the invention will generally comprise at least one anionic surfactant as well as an optional second surfactant which is selected from the group consisting of amphoteric/zwitterionic surfactant, nonionic or mixtures thereof. Preferably, the composition comprises an anionic or anionic surfactant and an amphoteric/zwitterionic.

The anionic surfactant which may be used may be aliphatic sulfonates, such as a primary alkane (e.g., $C_8-C_{22}$) sulfonate, primary alkane (e.g., $C_8-C_{22}$) disulfonate, $C_8-C_{22}$ alkene sulfonate, $C_8-C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}-C_{18}$ alkyl sulfate) or alkyl ether sulfate (including alkyl glyceryl ether sulfates). Among the alkyl ether sulfates are those having the formula:

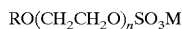

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium laurel ether sulfates are preferred.

The anionic may also be alkyl sulfosuccinates (including mono and dialkyl, e.g., $C_6-C_{22}$ sulfosuccinates); alkyl and acyl taurates, alkyl and acyl sarcosinates, sulfoacetates, $C_8-C_{22}$ alkyl phosphates and phosphates, alkyl phosphate esters and alkoxyl alkyl phosphate esters, acyl lactates, $C_8-C_{22}$ monoalkyl succinates and maleates, sulphoacetates, alkyl glucosides and acyl isethionates.

Sulfosuccinates may be monoalkyl sulfosuccinates having the formula:

$R^1O_2CCH_2CH(SO_3M)CO_2M$; and amide-MEA sulfosuccinates of the formula $R^1CONHCH_2CH_2O_2CCH_2CH(SO_3M)CO_2M$ wherein $R^1$ ranges from $C_8-C_{22}$ alkyl and M is a solubilizing cation.

Sarcosinates are generally indicated by the formula $RCON(CH_3)CH_2CO_2M$, wherein R ranges from $C_8-C_{20}$ alkyl and M is a solubilizing cation.

Taurates are generally identified by formula $R^2CONR^3CH_2CH_2SO_3M$ wherein $R^2$ ranges from $C_8-C_{20}$ alkyl, $R^3$ ranges from $C_1-C_4$ alkyl and M is a solubilizing cation.

Particularly preferred are the $C_8-C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 10% to about 35% by weight of the total bar composition. Preferably, this component is present from about 10% to about 30%.

The acyl isethionate may be an alkoxylated isethionate such as is described in Ilardi et al., U.S. Pat. No. 5,393,466, hereby incorporated by reference. This compound has the general formula

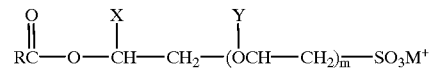

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

In general the anionic component will comprise from about 2 to 35% of the bar composition, preferably 10 to 30%.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

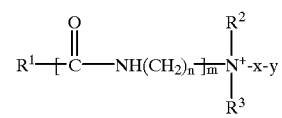

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

x is alkylene of 1 to 3 carbon atoms optionally substituted with hydroxyl, and y is $-CO_2-$ or $-SO_3-$ Suitable amphoteric detergents within the above general formula include simple betaines of formula:

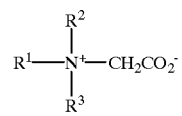

and amido betaines of formula:

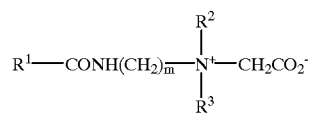

where m is 2 or 3.

In both formulae $R^1$ is alkyl or alkenyl of 7 to 18 carbons; and $R^2$ and $R^3$ are independently alkyl, hydroxyalkyl or carboxylalkyl of 1 to 3 carbons. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

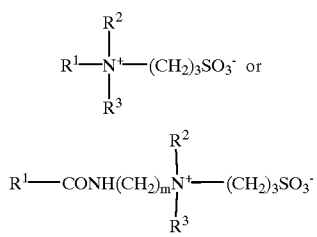

where m is 2 or 3, or variants of these in which —(CH$_2$)$_3$SO$_3^-$ is replaced by

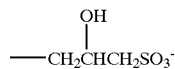

In these formulae R$^1$, R$^2$ and R$^3$ are as discussed for the amido betaine.

Amphoteric, if present, generally comprises 2% to 15% of the bar composition.

Other surfactants (i.e., nonionics, cationics) may also be optionally used although these generally would not comprise more than 0.01 to 10% b wt. of the bar composition.

Nonionic surfactants include in particular the reaction products of compounds having a hydrophobic group and a reactive hydrogen atom, for example, aliphatic alcohols, acids, amides or alkyl phenols with alkylene oxides, especially ethylene oxide either alone or with propylene oxide. Specific nonionic detergent compounds are alkyl (C$_6$–C$_{22}$) phenols-ethylene oxide condensates, the condensation products of aliphatic (C$_8$–C$_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference and polyhydroxyamides such as described in U.S. Pat. No. 5,312,954 to Letton et al., hereby incorporated into the subject application by reference.

Examples of cationic detergents are the quaternary ammonium compounds such as alkyldimethylammonium halogenides.

Other surfactants which may be used are described in U.S. Pat. No. 3,723,325 to Parran Jr. and "Surface Active Agents and Detergents" (Volume I & II) by Schwartz, Perry & Berch, both of which are also incorporated into the subject application by reference.

Polyalkylene Glycol

A second required component of the invention is polyalkylene glycol or mixture of polyalkylene glycols wherein the polyalkylene glycol is, for example, a polyethylene or polypropylene glycol. The polyalkylene glycols must have a MW of between greater than 300, preferably greater than about 350 and 1500 Dalton.

This MW range is important because at MW below the minimum 300 range, the PEG in bar does not significantly reduce the skin irritation potential caused by anionic surfactants (see Example 2, FIG. 2 and 3); and at MW above 1500, the PEG molecule is not as readily miscible with long chain fatty acid soaps, which are used as gelling agents. Also at MW above 1500, the PEG does not provide as much oily skin feel as a PEG with a lower molecular weight.

It is another important aspect of the invention that ratio of alkylene glycol to anionic is at least 1:1 and preferably 2:1 and greater. Again, at ratio below 1:1, the mildness is not readily felt (see Example 1, FIG. 1).

Generally, this compound or mixture of compounds will comprise 10% to 70% by wt. of the bar compositions.

Gelling Agent

A gelling agent is required in the compositions of the invention. While not wishing to be bound by theory, such component is believed required because the higher levels of low MW polyalkylene glycol required by the invention are in the form of liquid or paste. The gelling agent is believed needed to enhance bar integrity.

Examples of gelling agents include, but are not limited to:
(i) neutralized C$_8$ to C$_{25}$ carboxylic acid (soap), preferably neutralized C$_8$ to C$_{25}$ monocarboxylic acid (straight chain, saturated soap);
(ii) paraffin waxes, polyethylene waxes, petrolatum, greases, jellies, fumed silica and/or aluminosilicates, urea, and clay;

Examples of waxes which may be used include Paraffin Wax distributed by Whittaker, Clark & Daniels, Inc. and Luwax from BASF, and MULTIWAX Microcrytalline WAX from Witco. A preferred wax is glyceryl stearate.

Generally, the gelling agent will comprise 1 to 20% by wt. total composition.

Bar Moisture Level

Finally, bars of the invention use low levels of water, i.e., 2% to less than 10% by wt., preferably 2% to 8%, more preferably 3% to 7% by weight total composition. Water levels are kept purposefully in such a range to ensure homogenous, pumpable melts which, upon cooling, form rigid solids. Excess water will result in poor mixing, low viscosities and phase separation in the melt and unacceptably soft solids and mushiness when cooled.

Optional Structuring Aids and Fillers

Another optional component of the invention is the use of solid structuring aids and fillers, i.e., to maintain bar structural integrity. Examples of such structuring aids include, but are not limited to the following:
polyalkylene glycols having MW of 2500 to 10,000 and MP of about 40° C. to 65° C.; C$_8$ to C$_{20}$ alkanols, preferably straight chain, preferably saturated C$_{14}$ to C$_8$ alkanols; C$_8$ to C$_{25}$ fatty acids, preferably straight chain, preferably saturated C$_{14}$ to C$_{22}$ fatty acids; and water soluble starches, such as maltodextrin.

The structuring aids and fillers generally comprise 0% to 35% by weight of the bar composition, preferably 10% to 25% by weight.

Other Optional Ingredients

Other components which may be used in the bars of the invention are as follows:

Bars of the invention also generally incorporate 0 to 30% by wt., preferably 1 to 25% of a benefit agent in the bar composition.

The benefit agent "composition" of the subject invention may be a single benefit agent component or it may be a benefit agent compound added via a carrier. Further the benefit agent composition may be a mixture of two or more compounds one or all of which may have a beneficial aspect. In addition, the benefit agent itself may act as a carrier for other components one may wish to add to the bar composition.

The benefit agent can be an "emollient oil" by which is meant a substance which softens the skin (stratum corneum)

by increasing into water content and keeping it soft by retarding decrease of water content.

Preferred emollients include:

(a) silicone oils, gums and modifications thereof such as linear and cyclic polydimethylsiloxanes; amino, alkyl alkylaryl and aryl silicone oils;

(b) fats and oils including natural fats and oils such as jojoba, soybean, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin and derivatives thereof;

(d) hydrophobic plant extracts;

(e) hydrocarbons such as liquid paraffins, vaseline, microcrystalline wax, ceresin, squalene, pristan and mineral oil;

(f) higher fatty acids such as lauric, myristic, palmitic, stearic, behenic, oleic, linoleic, linolenic, lanolic, isostearic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins such as vitamin A and E, and vitamin alkyl esters, including those vitamin C alkyl esters;

(l) sunscreens such as octyl methoxyl cinnamate (Parsol MCX) and butyl methoxy benzoylmethane (Parsol 1789);

(m) phospholipids; and (n) mixtures of any of the foregoing components.

A particularly preferred benefit agent is silicone, preferably silicones having viscosity greater than about 10,000 centipoise. The silicone may be a gum and/or it may be a mixture of silicones. One example is polydimethylsiloxane having viscosity of about 60,000 centistokes.

All percentages mentioned above are intended to be by wt. unless otherwise indicated.

The following examples are meant for illustrative purposes only and are not intended to limit the claims in any way.

EXAMPLES

Methodology

Mildness Assessments

Zein dissolution test was used to preliminarily screen the irritation potential of the formulations studies. In an 8 oz. jar, 30 mLs of an aqueous dispersion of a formulation were prepared. The dispersion sat in a 45° C. bath until fully dissolved. Upon equilibration at room temperature, 1.5 gms of zein powder were added to each solution with rapid stirring for one hour. The solutions were then transferred to centrifuge tubes and centrifuged for 30 minutes at approximately 3,000 rpms. The undissolved zein was isolated, rinsed and allowed to dry in a 60° C. vacuum oven to a constant weight. The percent zein solubilized, which is proportional to irritation potential, was determined gravimetrically.

Formulation Processing (Cast-melt)

Bars were prepared by a cast melt process. First, the components were mixed together at 80–120° C. in a 500 ml beaker, and the water level was adjusted to approximately 10–15 wt. %. The batch was covered to prevent moisture loss and was mixed for about 15 minutes. Then the cover was removed, and the mixture was allowed to dry. The moisture content of the samples taken at different times during the drying stage and was determined by Karl Fisher titration with a turbo titrator. At the final moisture level (~5%), the mixture in the beaker (in the form of a free-flow liquid) was dropped into bar molds and was allowed to be cooled at room temperature for four hours. Upon solidification, the mixture was casted in the bar mold into a bar.

Example 1

The Impact of PEG (MW>300)/Anionic Ratio on Anionic Surfactant—Protein Interaction In the zein dissolution testing (FIG. 1), PEGs with molecular weight at 400 and above were found to significantly reduce the amount of zein protein dissolved by sodium acyl isethionate when the PEG to the anionic surfactant weight ratio was above 1:1, preferably above 2:1. Below this 1:1 PEG/anionic ratio, the benefit of zein-reduction by PEG was insignificant. These results show that, only at relatively high levels of addition, PEGs having molecular weight above 300 Dalton, preferably above about 350, function as skin moisturizer to reduce the surfactant skin interaction that leads to skin irritation.

Example 2

The Lack of Mildness Enhancement of PEG (MW≦300) on Anionic Surfactants

At and below molecular weight 300, PEGs and the presented water soluble nonionic monomers (i.e., ethylene glycol, propylene glycol, sorbitol, and glyceryl) do not significantly reduce the amount of zein protein dissolved by sodium acyl isethionate (FIG. 2) and sodium laurylether (3 EO) sulfate (FIG. 3). Therefore, there is a cut-off PEG molecular weight (around 300), below which PEG and those water soluble monomers are ineffective in reducing the surfactant protein interaction that may lead to skin irritation.

Example 3

Bar Formulations

The bar formulations 1–5 in Table 1 use anionic sodium acyl isethionate and sodium laurylether (3 EO) sulfate and amphoteric cocoamidopropyl betaine as the major detergents. Novel to the art, these bar compositions contain relatively high levels of low MW PEGs (MW between 400–1500) as moisturizer. PEG 1450 and PEG1000 in these ultra-mild bars (Formulation No. 1 to No. 4) promote rich and creamy lather.

In order to enhance the liquidish, non-occlusive type of moisturizing sensory cues, PEG 400 (having MW and melting temperature even lower than those of PEG 1450 and PEG 1000), is preferably used in Bar formulation No. 5

TABLE 1

Bar compositions containing relatively high levels of low MW PEGS.

| COMPOSITIONS | No. 1 Wt. % | No. 2 Wt. % | No. 3 Wt. % | No. 4 Wt. % | No. 5 Wt. % |
|---|---|---|---|---|---|
| Sodium Acyl Isethionate | 15.0 | 15.0 | 8.0 | 10.0 | 20.0 |
| Sodium Laurylether (3EO) Sulfate | 0.0 | 0.0 | 2.0 | 3.0 | ? |
| Cocoamidopropyl Betaine | 10.0 | 10.0 | 15.0 | 12.0 | 5.0 |
| Sodium Stearate | 12.0 | 15.0 | 15.0 | 9.0 | 12.0 |
| PEG 1450 | 35.5 | 18.5 | 40.0 | 30.0 | ? |
| PEG 1000 | 0.0 | 0.0 | 0.0 | 12.0 | ? |
| PEG 8000 | 15.0 | 29.0 | 5.0 | 7.0 | 12.0 |
| Fatty Acid | 4.0 | 4.0 | 9.5 | 4.5 | 10.0 |
| Paraffin Wax | 3.0 | 3.0 | 0.0 | 7.0 | 5.0 |
| Water | 5.5 | 5.5 | 5.5 | 5.5 | 4.0 |

What is claimed is:

1. A skin cleansing bar composition comprising:
   (a) 2% to 35% by wt. acyl isethionate;
   (b) 0 to 20% by wt. amphoteric, zwitterionic, or nonionic surfactant or mixtures thereof;
   (c) 10% to 70% by wt. of polyalkylene glycols having molecular weight of greater than 300 to less than 1000; weight ratio of (c) to (a) being greater than 2:1;
   (d) greater than about 1% to 20% by wt. of gelling agents;
   (e) 2% to less than 10% water;.

2. A composition according to claim 1(d), in which the gelling agents are selected from the group consisting of $C_8$ to $C_{25}$ neutralized carboxylic acids (soap), paraffin waxes, polyethylene waxes, glyceryl stearate, petrolatum, greases, jellies, fumed silica, alumino silicates, urea, clay and mixtures thereof.

3. A composition according to claim 1, wherein 0% to 35% by weight of solid structurants and fillers selected from the group consisting of $C_8$ to $C_{25}$ fatty acids, $C_8$ to $C_{20}$ alkanols, water soluble starches (i.e., maltodextrin), polyalkylene glycol having molecular weight between 2500 and 10000, and mixtures thereof are included.

4. A composition according to claim 1(a), wherein the acyl isethionate comprises 10% to 30% by wt. total composition.

5. A composition according to claim 1(b), wherein the amphoteric and zwitterionic surfactants comprise 2% to 15% by wt. total composition.

6. A composition according to claim 1(c), wherein the low molecular weight polyalkylene glycol has the following structure

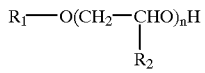

wherein $R_1$=H, $C_1$ to $C_4$ alkyl;

$R_2$=H, $CH_3$; and n is greater than 6 and less than 35.

7. A composition according to claim 2, wherein the neutralized fatty acid (soap) is a straight chain, saturated, $C_{12}$–$C_{22}$ neutralized monocarboxylic acid.

8. A composition according to claim 3, wherein the structurant is $C_8$ to $C_{25}$ carboxylic fatty acid, and the fatty acid comprises 5% to 25% by weight of the total composition.

9. A composition according to claim 3, wherein the structurant is fatty acid, and fatty acid is a straight chain, saturated $C_{12}$ to $C_{22}$ monocarboxylic acid.

10. A composition according to claim 3, wherein the alkanol is cetyl alcohol.

* * * * *